(12) United States Patent
Spolaczyk et al.

(10) Patent No.: US 7,102,131 B2
(45) Date of Patent: Sep. 5, 2006

(54) DEVICE FOR PHOTOMETRIC MEASUREMENT OF SEVERAL SAMPLES

(75) Inventors: Reiner Spolaczyk, Hamburg (DE); Andreas Maass, Hamburg (DE); Rainer Treptow, Norderstedt (DE)

(73) Assignee: Eppendorf AG, Hamburg (DE)

( * ) Notice: Subject to any disclaimer, the term of this patent is extended or adjusted under 35 U.S.C. 154(b) by 442 days.

(21) Appl. No.: 10/476,848

(22) PCT Filed: Jun. 27, 2002

(86) PCT No.: PCT/EP02/07120

§ 371 (c)(1),
(2), (4) Date: Nov. 3, 2003

(87) PCT Pub. No.: WO03/002991

PCT Pub. Date: Jan. 9, 2003

(65) Prior Publication Data

US 2004/0141178 A1    Jul. 22, 2004

(30) Foreign Application Priority Data

Jun. 29, 2001 (DE) ............................... 101 31 687

(51) Int. Cl.
*G01N 21/64* (2006.01)
(52) U.S. Cl. .................................. 250/339.12; 356/417
(58) Field of Classification Search ........... 250/339.12, 250/339.08, 458.1, 459.1, 236; 356/213, 356/417, 418
See application file for complete search history.

(56) References Cited

U.S. PATENT DOCUMENTS 4,343,991 A    8/1982    Fujiwara et al.
4,628,026 A *  12/1986   Gardell et al. ............. 435/7.24
5,038,258 A    8/1991    Koch et al.
5,294,799 A    3/1994    Aslund et al.
5,427,920 A *  6/1995    Berndt et al. ................ 435/34
5,482,861 A *  1/1996    Clark et al. .................. 436/48
5,500,188 A *  3/1996    Hafeman et al. ...... 204/403.01

(Continued)

FOREIGN PATENT DOCUMENTS

EP    0 902 271 A2    3/1999

OTHER PUBLICATIONS

WO 01/35079 A1, Fluorometer with Low Heat-Generating Light Source, Publication Date: May 17, 2001.

(Continued)

*Primary Examiner*—David Porta
*Assistant Examiner*—Faye Boosalis
(74) *Attorney, Agent, or Firm*—Rankin, Hill, Porter & Clark LLP

(57) ABSTRACT

A device for photometric measurement of several samples (12) that are exposed to radiation from a light source (14) associated therewith. The light modified by the samples (12) is intercepted by an optical device (19) and is guided as a sum of all the light radiated from all samples (12) to at least one sensor (27) for measuring the intensity and evaluation thereof in an evaluation device (32) arranged downstream. The light sources (14) are controlled individually by a control device (31) and the evaluation device (32) and the control device (31) are controlled such that the evaluation device (32) separates the light from each sample (12) from the light of the other samples. The control device (31) modulates the light source (14) with various signals, which are pre-assigned to the evaluation device (32) and used to determine the light signals of the individual samples (12) from the sum signal received by the sensor (27).

15 Claims, 1 Drawing Sheet

U.S. PATENT DOCUMENTS

| | | | |
|---|---|---|---|
| 5,710,628 A | * | 1/1998 | Waterhouse et al. ........ 356/344 |
| 5,825,478 A | * | 10/1998 | Wilcox et al. ................ 356/73 |
| 5,942,432 A | * | 8/1999 | Smith et al. ............. 435/303.1 |
| 5,959,738 A | * | 9/1999 | Hafeman et al. ........... 356/440 |
| 6,034,774 A | * | 3/2000 | Marcus et al. .............. 356/511 |
| 6,043,880 A | * | 3/2000 | Andrews et al. ............ 356/311 |
| 6,097,025 A | * | 8/2000 | Modlin et al. ......... 250/227.22 |
| 6,104,945 A | * | 8/2000 | Modell et al. .............. 600/473 |
| 6,122,042 A | * | 9/2000 | Wunderman et al. ......... 356/73 |
| 6,940,598 B1 | * | 9/2005 | Christel et al. ............. 356/417 |
| 6,965,105 B1 | * | 11/2005 | Oldham et al. ............. 250/236 |

OTHER PUBLICATIONS

Hauser P C et al: "A Solid-State Instrument for Fluorescence Chemical Sensors Using a Blue Light-Emitting Diode of High Intensity", Measurement Science and Technology.

* cited by examiner

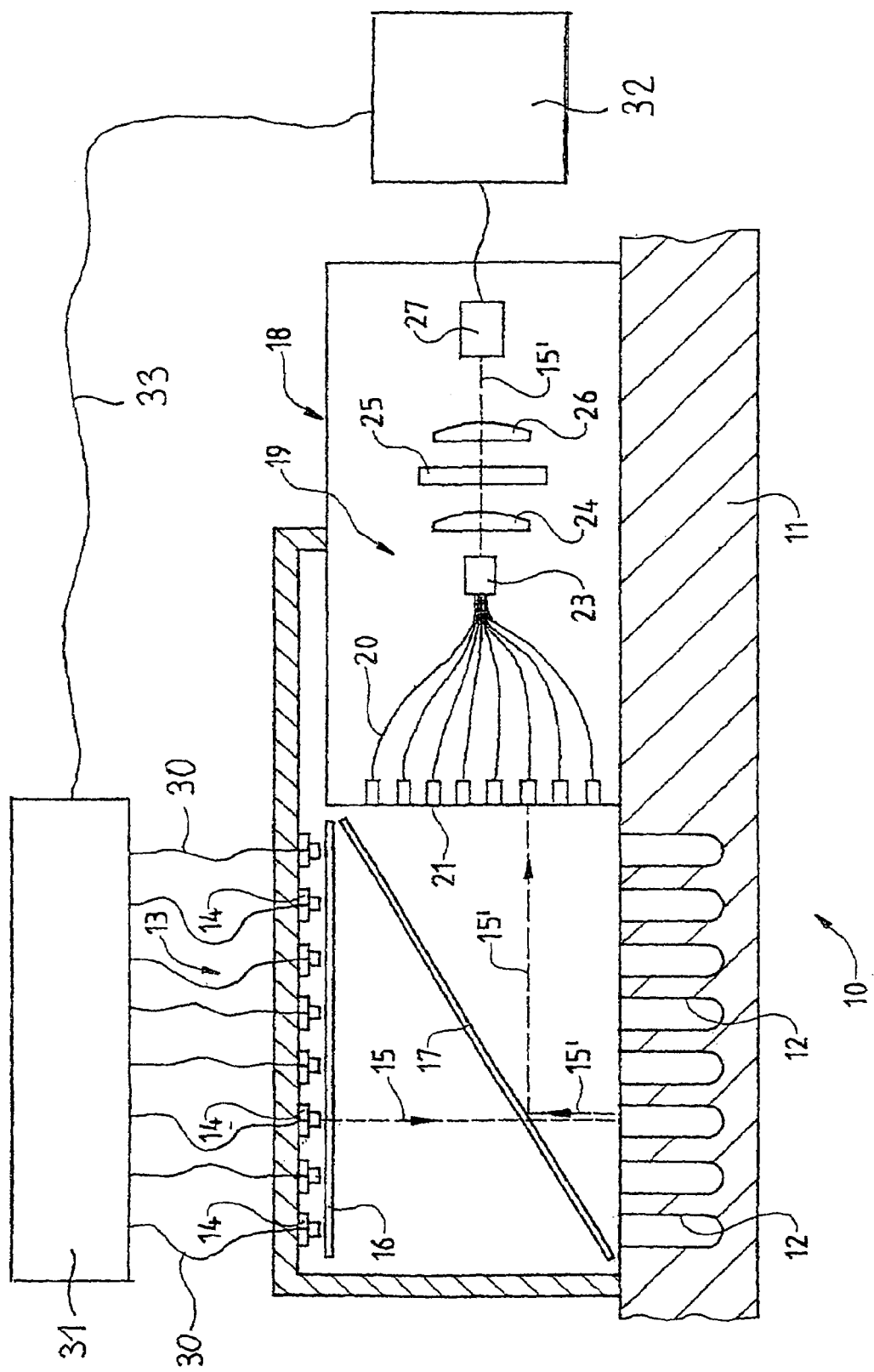

DEVICE FOR PHOTOMETRIC MEASUREMENT OF SEVERAL SAMPLES

BACKGROUND OF THE INVENTION

The present invention relates to an apparatus for photometrically testing several specimens (12) that are each irradiated by an associated light source. An apparatus of this type is used to photometrically test several specimens, for instance on-line on a thermocycler, in order to monitor the progress of PCR procedures. However, such an apparatus is also used to test a plurality of microarray spots on glass slides, or as well wherever a plurality of specimens must be tested photometrically by means of fluorescence, absorption, scattering phenomena, and the like. When testing fluorescence specimens, an appropriate fluorescence indicator is added as a rule.

Such an apparatus, however, incurs the drawback of entailing a plurality of light paths, which, in turn, require a complex design. When only one light path is used between a light source and a light sensor, then the specimens must be moved sequentially into the light path and substantial mechanisms are entailed. It is furthermore known to move the light, such as a reflected light, over stationary specimens. Unfortunately, this design incurs the same drawbacks as above.

On the other hand, to simultaneously irradiate all specimens simultaneously by the same light source and to view them individually using several sensors would be exceedingly costly. This is due, in part, to the fact that the sensors are much more expensive than light sources.

Accordingly, the patent documents EP 0902271 A2 and WO 01/35079 A1 propose individually irradiating the specimens using associated light sources and to use only one light sensor to determine and analyze the light from all specimens, namely the summed signal.

This solution, however, raises the problem of identifying the light intensities of the particular specimens from the summed signal picked up by the sensor. The state of the art disclosed by both of the above patent documents solves this problem in that the different light sources are operative only individually, so that only the light from a given specimens will fall on the sensor which only receives a single specimen's light that, provided there be appropriate synchronization, can be allocated to the particular specimen.

However such apparatus suffers from drawbacks because, assuming there are n specimens, each specimen may be illuminated at most only 1/n of the available measuring time. The values related to the particular specimens are available only within short time intervals. Moreover, the measured signal cannot be integrated over a substantial length of time, illustratively when the signal is weak, to still attain in this manner a good signal to noise ratio. If the signal fluctuates, or when ascertaining the progress of a reaction in the specimens, it will be impossible to monitor the signal as a function of time.

SUMMARY OF THE INVENTION

Therefore, it is an object of the present invention to design an apparatus of the above kind such that the specimens can be measured over comparatively long time intervals.

In accordance with the invention, all specimens are constantly illuminated and analyzed. The illumination is carried out using differently modulated signals, the summed signal transmitted by the sensor being resolvable into the individual signals when knowing the different modulations of the signals provided the different signals do differ sufficiently. The summed light from the specimens may be analyzed by one or more sensors that analyze, for instance, different effects appearing in the light. The light sources are individually driven by a control unit. Alternatively, the control unit may be in the form of several control units individually associated with the light sources. Individual light source control allows driving the light sources individually or in groups, illustratively one group of identical specimens being irradiated with the same signal modulation. The signal modulation must be known to the analyzer to allow the analyzer to analyze the individual signals. Illustratively, such knowledge may be implemented by permanently programming into the analyzer the modulations being used or by transmitting the modulations from the control unit. Under particular default conditions, the analyzer also may itself retrieve the modulations. A substantial advantage is offered by the feasibility of permanently acquiring the signals from all specimens, whereby these signals may, for instance, be integrated over long time intervals or be monitored regarding their changes with time. The apparatus of the invention is applicable to all optical measurement procedures concerning specimen analysis such as measuring fluorescence, transmission, light scattering, and the like. The apparatus may be used for on-line specimen determination on thermocyclers (for PCR), chip readers, MTP readers, spot readers, and other multi-analytical test means.

In further accordance with the present invention, the signals are square. This creates advantages in circuitry and also regarding signal analysis. Particularly, square signals offer the advantage of digitized signal generation.

The signals must appropriately differ in their modulations. Illustratively, they may differ with respect to phase. However, in accordance with the present invention, the signal modulations differ in their frequencies. The individual signals may be separated in the analyzer using, for instance, appropriate frequency filters. The circuits required are comparatively simple.

Alternatively, and in further accordance with the present invention, the signals differ in their code sequence. Using appropriate decoding algorithms, the individual signals may be retrieved from the summed signal. Advantageously, the signals are mutually orthogonal to allow clean signal separation even for a plurality of such signals, such as when several hundred specimens must be analyzed.

In further accordance with the present invention, the control unit generates the frequencies according to a specific algorithm from a single mother clock timing and the analyzer, using the algorithm, generates the frequencies required for analysis from the same mother clock timing procedure. In this manner many different frequencies may be generated in highly accurate and precise manner, both to drive the light sources and to analyze the summed signal.

Frequency-discriminated signals may be retrieved by individually multiplying the summed signal with each particular signal frequency and by subsequent lowpass filtering. However, in further accordance with the present invention, the analyzer retrieves the individual signals out of the summed signal by Fourier transforms and by determining the amplitudes of the individual signal frequencies. Signal frequency analysis of the individual specimens from the summed signal by Fourier transformation is highly accurate and precise and its circuitry is easily implemented.

The suitable light sources may be all those fit for photometry that may selected depending on the requirements on light, for instance for fluorescence purposes—or depending on the requirements set on the light path—for instance sharp focusing on one of several specimens—or regarding light intensity or also the rate of modulation. Accordingly, both incandescent bulbs and laser, flash and other light sources are applicable. Advantageously, however, the light sources are light emitting diodes or LEDs. LEDs or laser diodes are economically available while offering appropriate light quality and are characterized by being easily integrated and mounted, for instance as an array on a printed circuit board.

Preferably, light sources are selected such that the light radiated by them is able to excite selected fluorescence colors.

In further accordance with the present invention, a filter to eliminate interfering light is configured in the downstream direction of the radiation of the light sources. A short wavelength filter is used in fluorescence measurements to filter out light of long-wave lengths, in particular in the region of the fluorescence light. Bandpass filters also are suitable.

In accordance with another aspect of the invention, light from the specimens to the sensor is deflected by a dichroic beam splitter transmitting the light from the light sources. The dichroic beam splitters further improve the separation between the short wavelength light of illumination and the long wavelength light of fluorescence.

In accordance with another aspect of the invention, the optical device includes comprises several optical-guides/fibers of which the light entry surfaces are mutually spaced and parallel and of which the light exit surfaces are adjacent and parallel. The collimator required to collect the light radiated from the specimens and transmitting it to the light sensor may be improved for instance with respect to the conventional lens element collimator, especially as regards the parallelism of the light incident on the sensor. This high parallelism is especially advantageous when the sensor would be susceptible at its input to deviations from the light's parallelism, for instance when being fitted at the input with an interference filter.

In further accordance with the present invention, a filter eliminating interfering light is situated in front of the sensor. As regards fluorescence measurements, the filter is a long wavelength filter eliminating residual short wavelength portions of the light illustratively arising as scattered light from the light sources. Bandpass filters are also appropriate for these purposes.

Further, the specimens may be configured in wells of a thermocycler and may be tested photometrically on a thermocycler for the purpose of optimizing a PCR procedure carried out on the thermocycler.

BRIEF DESCRIPTION OF THE DRAWING

These and further features of the invention will be apparent with reference to the following description and single drawing FIGURE, which illustrates the preferred embodiment of the inventive apparatus.

DETAILED DESCRIPTION OF THE PREFERRED EMBODIMENTS

The apparatus 10 comprises a schematic, conventional thermocycler 11 with wells 12. Reaction vials (not shown) are in place in the wells 12. Each vial contains one PCR batch with one or more fluorescence indicators.

A covered housing 13 fitted with an illumination unit of several LEDs 14 is set on the thermocycler 11. One LED 14 is allocated to each well 12. Preferably, the LEDs 14 are configured as an array. Each LED 14 points in a direction such that it will irradiate only one associated well 12 and, if possible at all, not the adjacent wells. The LEDs 14 may, in particular, be laser diodes.

An illustrative light path is denoted by 15, 15'. The light 15 is radiated from the LED 14 and first passes through an optional, but preferred, short wavelength filter 16 by means of which long wavelength components are filtered out. Then the light 15 passes through a beam splitter 17, which, in this instance, preferably shall be wholly transmitting.

The light 15 radiated from the LED 14 will excite a fluorescence indicator contained in a PCR batch in the well 12. The indicator, in turn, emits a fluorescence signal 15'. The beam splitter 17 is designed such that the fluorescence signal 15' is reflected laterally.

A dichroic mirror is preferably used as the beam splitter 17 and will transmit the excitation light while reflecting the emitted, longer wavelength fluorescence signal.

The reflected fluorescence signal 15' is then sensed by a detector 18. The detector 18 is fitted with an optical device 19 that can reproduce the fluorescence signal 15' onto a light sensitive sensor 27.

In lieu of the typical large-area lens element, the collimator in the optical device 19 is an array of optic fibers 20. The optical fiber array catches the light from the wells 12 reflected by the beam splitter 17 by means of the mutually spaced light input areas 21 and harnessing optic fibers so as to transmit the light through parallel harness ends at 23.

Contrary to a collimator composed of lens elements, the collimator configuration of a bundle of optic fibers 20 offers the feature that the light exiting the bundle optic fibers at 23 is collimated more narrowly. That feature is especially advantageous when, for instance, interference filters offering a spectral transfer function that depends on the light's angle of incidence are configured subsequently.

Next, the fluorescence signal 15' is reproduced through the optic fibers harness 23, through a lens element 24, through a long wavelength filter 25, and a further lens element 26 onto a sensor 27. The long wave pass filter 25 is required in order to filter any shorter wavelength regions out of the excitation light.

The design of the shown embodiment mode of the present invention is comparatively simple and economical.

In the event that several fluorescence indicators in the PCR batch must be tested, a further beam splitter may be configured in the region of the optical devices 19, for instance, after the long wavelength filter 25, to transmit one of the two fluorescence signals while reflecting the other. If one photo-sensitive sensor is mounted in the corresponding light paths, then two or even more fluorescence signals may be processed with further beam splitters.

Where several fluorescence indicators are present, a bandpass filter may be additionally present before the sensor in order to transmit the emission range of the particular indicator and to block that of the other indicators. Conceivably as well, and for the purpose of limiting the number of required sensors, exchangeable bandpass filters may be used.

To compensate for thermal effects, the apparatus of the present invention may comprise a reference light path running analogously to the path 15, 15' except that the LED associated to the reference light path does not illuminate a PCR batch, but rather a reference surface. The light reflected from the surface is analyzed by the detector and the variations incurred during PCR are used to correct the test values.

In the above shown embodiment of the present invention, the light sources are the LEDs 14. However, other appropriate light source may also be used.

In the above discussed embodiment, the specimens to be photometrically tested are configured in the wells 12 of a thermocycler 11. However, the apparatus of the invention also may be used when testing other specimens, illustratively in the form of micro-array spots on a glass plate. In this case, too, it will be the fluorescence effect, which, as a rule, will be utilized.

However, optical effects other than the fluorescence effect also may be photometrically determined in tested specimens, for instance transmission, light scattering, and the like. For that purpose, the light paths may be modestly modified but the basic design of the above shown embodiment mode will be preserved.

As shown by the single appended drawing, the light sources in the form of the LEDs 14 are individually connected by leads 30 to a control unit 31. In the state of the art, the control unit would individually drive the LEDs 14 such that only one of the LEDs 14 would be illuminated at a given time. In this case the sensor 27 only receives the light from one specimen of those configured in the wells 12. In the conventional case, an analyzer 32 following the sensor 27 and illustratively synchronized through a line 23 may unambiguously associate the received light with one of the wells 12.

However, this known timed control of the LEDs 14 entails the drawback that the wells 12 are irradiated at different times over only very short time intervals.

Accordingly, in the present invention, the control unit 31 is designed such that all diodes 14 are driven simultaneously whereby the analyzer 32 constantly receives signals from all wells 12 and is able to monitor the signals over a long time interval or, illustratively, may integrate the test values of the individual specimens into a mean value.

In order for the analyzer to discriminate between the individual specimens in the wells 12, the control unit is designed to modulate the light of all diodes 14 by means of different signals. Modulation is preferably amplitude modulation and the applied modulation signals are preferably square. This feature allows simple digital generation and digital analysis of the signals. Instead of the shown control unit 31, separate individual control units also may be used, which are individually associated with the LEDs 14. The LEDs 14 may be driven individually or, in special cases, in groups.

In one preferred embodiment, the individual signals differ in their frequencies. Accordingly, each LED 14 is modulated at a different frequency.

If the analyzer 32 knows the frequencies being used (for instance being permanently programmed into it), then the analyzer shall be able, by means of known algorithms, to filter the individual signals out of the summed light signal from all wells 12 acquired by the sensor 27, for instance by use of appropriate frequency filters.

However, the frequencies are preferably communicated from the control unit 31 through the cable 33 to the analyzer 32. Especially in the case of many frequencies close to one another, the best approach is to generate the frequencies in the analyzer 31 from a master clock and a specific algorithm (for instance a frequency division procedure). The timing from the master clock may then be applied through the cable 33 to the analyzer 32, which is able to generate the frequencies according to the same algorithm. In this manner optimal synchronization may be attained.

An appropriate way to filter the signals from the various wells 12 out of the summed signal of all specimens picked up by the sensor 27 consists in subjecting the summed signal in the analyzer 32 by means of appropriate circuitry to a Fourier analysis and then to retrieve the amplitudes corresponding to the signal of the particular wells 12 at the various frequencies of the individual signals.

When all LEDs 14 are driven simultaneously, a signal may be modulated on all LEDs that will differ for each LED from the signal of the other LEDs by the code sequence. The most appropriate square signals for this purpose for instance may be 1-1-0-1-1-0-1 . . . or 1-0-1-1-0-0-0-1,,, Advantageously, especially with respect to a very large number of specimens or wells 12, the signals shall be mutually orthogonal. The signals may be repeated at different code sequences in a fixed cycle. The signals also are being applied by the control unit 31 through the line 33 to the analyzer 32, which multiplies the summed signal of the sensor 27 from the different codes by the individual codes and, in this manner, is able to determine the amplitudes from the particular wells 12.

The invention claimed is:

1. An apparatus for photometrically testing several specimens (12) that are each irradiated by an associated light source (14), the light, which is altered by the specimens (12), being detected by an optical device (19) and being fed as a sum of the light radiated from all the specimens (12) to at least one sensor (27) for intensity determination and analysis in an analyzer (32) following said sensor, the light sources (14) being driven individually by a control unit (31), the analyzer (32) as well as the control unit (31) being controlled such that the analyzer (32) determines the light from each specimen (12) separately from the light of other specimens, wherein the control unit (31) modulates the light sources (14) with different signals that are fed as specific defaults into the analyzer (32) to determine, from the summed signal received by the sensor (27), by means of said analyzer, the light signals altered by the individual specimens (12).

2. The apparatus as claimed in claim 1, wherein the signals are square.

3. The apparatus as claimed in claim 1, wherein the signals differ in their frequencies.

4. The apparatus as claimed in claim 3, wherein the control unit (31) generates the frequencies according to a specific algorithm from a single mother clock timing and wherein the analyzer (32), using said algorithm, generates the frequencies required for analysis from said same mother clock timing procedure.

5. The apparatus as claimed in claim 3, wherein the analyzer (32) retrieves the individual signals out of the summed signal by Fourier transforms and by determining amplitudes of the individual signal frequencies.

6. The apparatus as claimed in claim 1, wherein the signals differ in their code sequences.

7. The apparatus as claimed in claim 1, wherein codes of all signals are mutually orthogonal.

8. The apparatus as claimed in claim 1, wherein the light sources are Light Emitting Diodes (14).

9. The apparatus as claimed in claim 1, wherein the light sources (14) are selected such that the light radiated by said light sources excites selected fluorescence colors.

10. The apparatus as claimed in claim 1, wherein a filter (16) to eliminate interfering light is configured downstream of the radiation of the light sources (14).

11. The apparatus as claimed in claim 1, wherein the light from the specimens (12) to the sensor (27) is deflected by a dichroic beam splitter (17) transmitting the light from the light sources (14).

12. The apparatus as claimed in claim 1, wherein the optical device (19) comprises several optical-guides/fibers

(20) of which a light entry surfaces (21) are mutually spaced and parallel and of which a light exit surfaces are adjacent and parallel.

13. The apparatus as claimed in claim 1, wherein a filter (25) eliminating interfering light radiated from the specimens precedes the sensor (27).

14. The apparatus as claimed in claim 1, wherein the specimens are disposed in wells (12) of a thermocycler (11).

15. An apparatus for photometrically testing several specimens comprising:

a plurality of light sources, each for simultaneously irradiating one of the several specimens;

an optical device for detecting the light reflected from the irradiated several specimens;

a sensor for receiving a combined sum of all of the reflected light detected by the optical device;

an analyzer, located following the sensor, for light intensity determination and analysis;

a control unit for individually controlling the plurality of light sources, wherein the analyzer as well as the control unit are controlled such that the analyzer determines the light from each specimen separately from the light of other specimens, and wherein the control unit modulates the plurality of light sources with different signals that are fed as specific defaults into the analyzer to determine, from the summed signal received by the sensor, by means of the analyzer, the light signals from each individual specimen.

* * * * *